US00PP37679P2

(12) United States Plant Patent
Cho

(10) Patent No.: US PP37,679 P2
(45) Date of Patent: Sep. 8, 2026

(54) ***COLOCASIA* PLANT NAMED 'Tropical Paradise'**

(50) Latin Name: *Colocasia esculenta*
Varietal Denomination: Tropical Paradise

(71) Applicant: John J. Cho, Kula, HI (US)

(72) Inventor: John J. Cho, Kula, HI (US)

( * ) Notice: Subject to any disclaimer, the term of this patent is extended or adjusted under 35 U.S.C. 154(b) by 0 days.

(21) Appl. No.: 19/437,281

(22) Filed: Dec. 30, 2025

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP21,995 P2 * 6/2011 Strode ..... A01H 6/10 Plt./373
PP28,567 P2 * 10/2017 Cho ..... A01H 6/10 Plt./373

OTHER PUBLICATIONS

Plant Development services website-citation for "Tropical Paradise". https://plantdevelopment.com/introductions/colocasia-royal-hawaiian-tropical-paradise/. 6 pages. (Year: 2026).*

* cited by examiner

*Primary Examiner* — Karen M Redden
(74) *Attorney, Agent, or Firm* — Weatherly IP Solutions, LLC; James M. Weatherly

(57) ABSTRACT

A new variety of *Colocasia* plant named 'Tropical Paradise' that is characterized by its broad spreading clumping and basal branching habit', initially 1 m in height and spread and achieving a mature height of 1.2 m and spread of 2 m when grown in moist soils. 'Tropical Paradise' exhibits large rounded sagittate leaves whose adaxial surfaces are glossy in texture and bright light green in background color, overlaid with contrasting dark green variegated flecks and patches in a variety of shapes and sizes. The earlier leaves of 'Tropical Paradise' are borne on burgundy colored petioles which exhibit narrow dark purple to black longitudinal streaks and stripes. As the leaves age, the purple-black striped variegation becomes dominant in the petioles.

3 Drawing Sheets

Genus and species: *Colocasia esculenta.*
Variety denomination: 'Tropical Paradise'.

BACKGROUND OF THE NEW PLANT

The present invention relates to a new and distinct variety of *Colocasia* commonly known as the taro plant or elephant ears. *Colocasia* is grown as a food crop or for use as an ornamental plant for planting in containers or in the landscape. The new variety is known botanically as *Colocasia esculenta* and will be referred to hereinafter by the variety name 'Tropical Paradise'.

*Colocasia* is a tuberous rooted perennial aroid which is native to tropical Asia and Polynesia. Native plants of *Colocasia* grow to 1.2 m to 2 m in height from starchy tubers. The leaves of *Colocasia* are heart-shaped and typically are very large in size. *Colocasia* are also grown as an ornamental plant for the landscape in warmer climates or as a summer container plant in colder areas with warm summers. The new *Colocasia* variety named 'Tropical Paradise' is the product of a formal long-term breeding program carried out in a cultivated area in Kula, Hawaii. The purpose of the breeding program is to develop new commercial varieties by combining attributes not found in currently commercially available varieties, especially novel colors and patterns of leaves and their petioles.

'Tropical Paradise' is a seedling selection from the controlled pollination of two unreleased and unpatented varieties raised during the breeding program, namely breeding line 'FO7' as the male parent, and breeding line 'MG-Mojito' as the female parent. Seeds were allowed to mature within the developing fruits that formed after pollination. Seeds were removed around 45 days after pollination, and sown. From the resulting seedlings, the inventor selected 'Tropical Paradise' in 2021. The inventor selected 'Tropical Paradise' in 2021 in his growing grounds in Kula, Hawaii for its combination of prolific basal branching, large, variegated leaves, and contrastingly variegated petioles.

Propagation. The most commonly employed means of asexual propagation of the genus *Colocasia* is the excision and replanting of a shoot which consists of the apical 1 cm to 2 cm portion of the plant corm with the attached basal 15 cm to 20 cm portion of the petiole. In regions of the world where *Colocasia* is grown, this plant shoot is known as a "huli", and the means of propagation is known as "huli propagation".

Asexual propagation of 'Tropical Paradise' was first carried out by the inventor in 2021 at the inventor's growing grounds in Kula, Hawaii, using the method of huli propagation. The inventor observed that the newly propagated plants, and all subsequently propagated plants have confirmed that the unique features of 'Tropical Paradise' are fixed and stable, and that 'Tropical Paradise' reproduces true to type in successive generations of asexual propagation.

SUMMARY

The following traits have been repeatedly observed and represent the distinguishing characteristics of the new *Colocasia* variety named 'Tropical Paradise'. 'Tropical Paradise' has not been tested under all possible conditions and phenotypic differences may be observed with variations in environmental, climatic and cultural conditions, however, without any variance in genotype:

1. 'Tropical Paradise' grows with a broad clumping habit', initially 1 m in height and spread and achieving a mature height of 1.0 m-1.2 m and spread of 2 m when grown in moist soils.
2. Plants of 'Tropical Paradise' exhibit prolific basal branching with high numbers of petioles and leaves.
3. 'Tropical Paradise' exhibits large rounded sagittate leaves.
4. The early leaves of 'Tropical Paradise' are borne on burgundy colored petioles which exhibit dark purple to black longitudinal streaks and stripes.
5. The leaf tissue on the leaf adaxial surface, opposite the point of petiole attachment to the abaxial surface, and known as the piko, is lightly red-purple in color on the adaxial surface only.
6. The adaxial surfaces of the leaves of 'Tropical Paradise' are glossy in texture and bright light green in background color, overlaid with contrasting dark green variegated flecks and patches in a variety of shapes and sizes.

DESCRIPTION OF THE PHOTOGRAPHS

The three accompanying color photographs illustrate the overall appearance of 'Tropical Paradise' showing the colors as true as it is reasonably possible to obtain in colored reproductions of this type. Colors in the photographs may differ from the color values cited in the detailed botanical description, which accurately describe the actual colors of the new variety 'Tropical Paradise'.

All photographs were taken in mid-September 2025 from a plant which was growing in-ground outdoors in Santa Barbara, California. The illustrated plant was planted as a young liner plant in July 2024 and has not received any winter protection or been treated with any plant growth regulators.

DESCRIPTION OF THE NEW VARIETY

Figure 1:
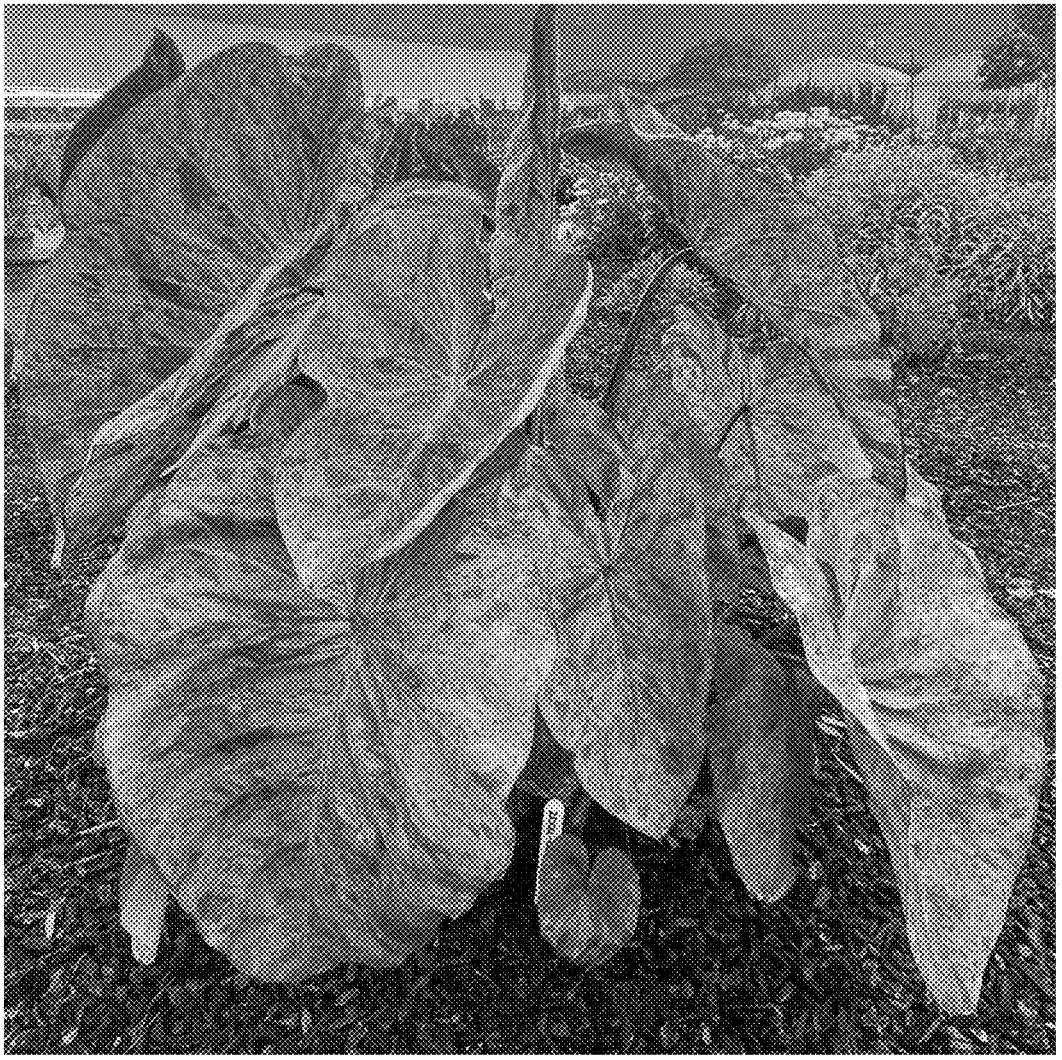
FIG. 1 shows a mature whole plant of 'Tropical Paradise' growing in-ground.
Figure 2:
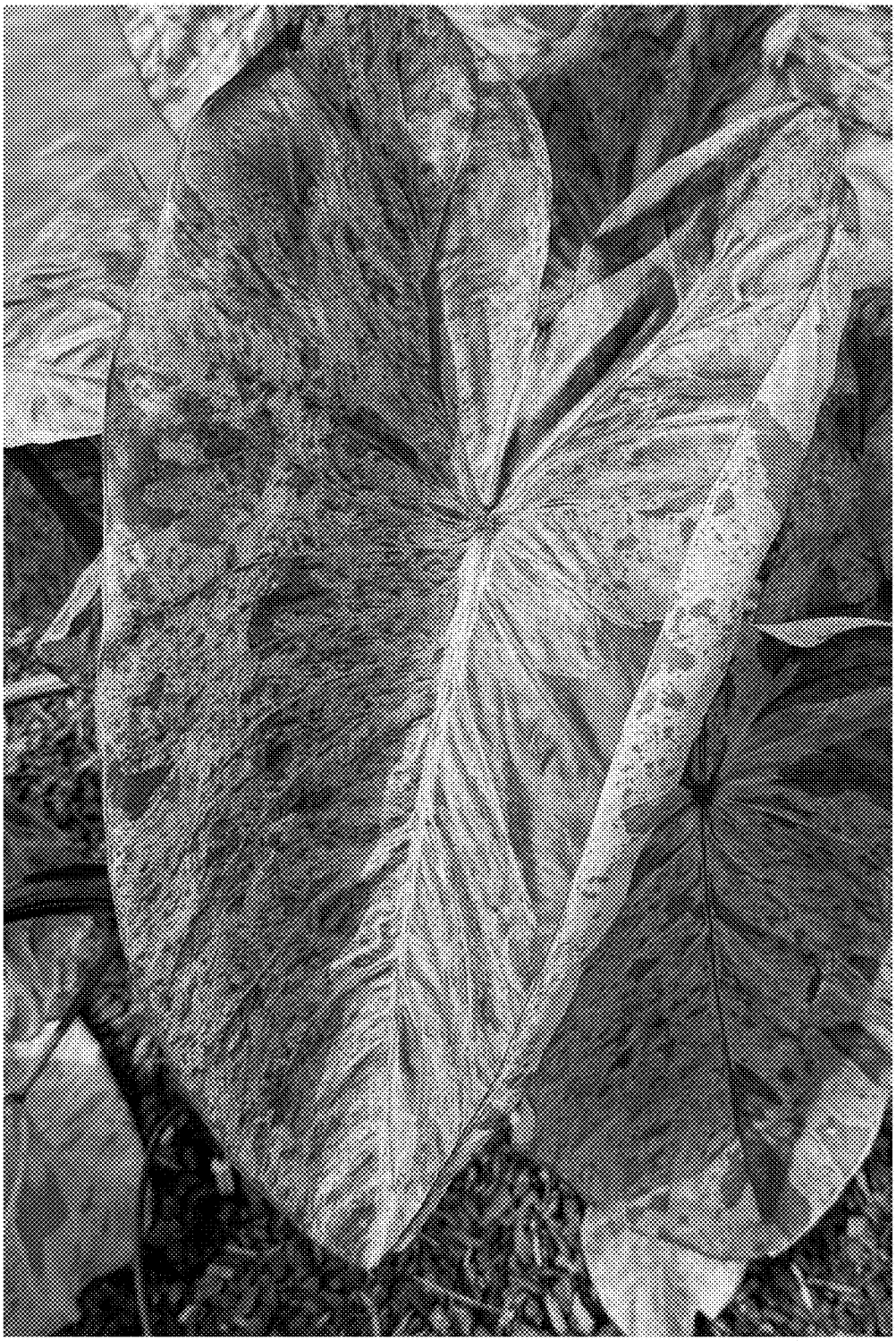
FIG. 2 shows a close-up view of the typical adaxial surface of a young leaf of 'Tropical Paradise'.
Figure 3:
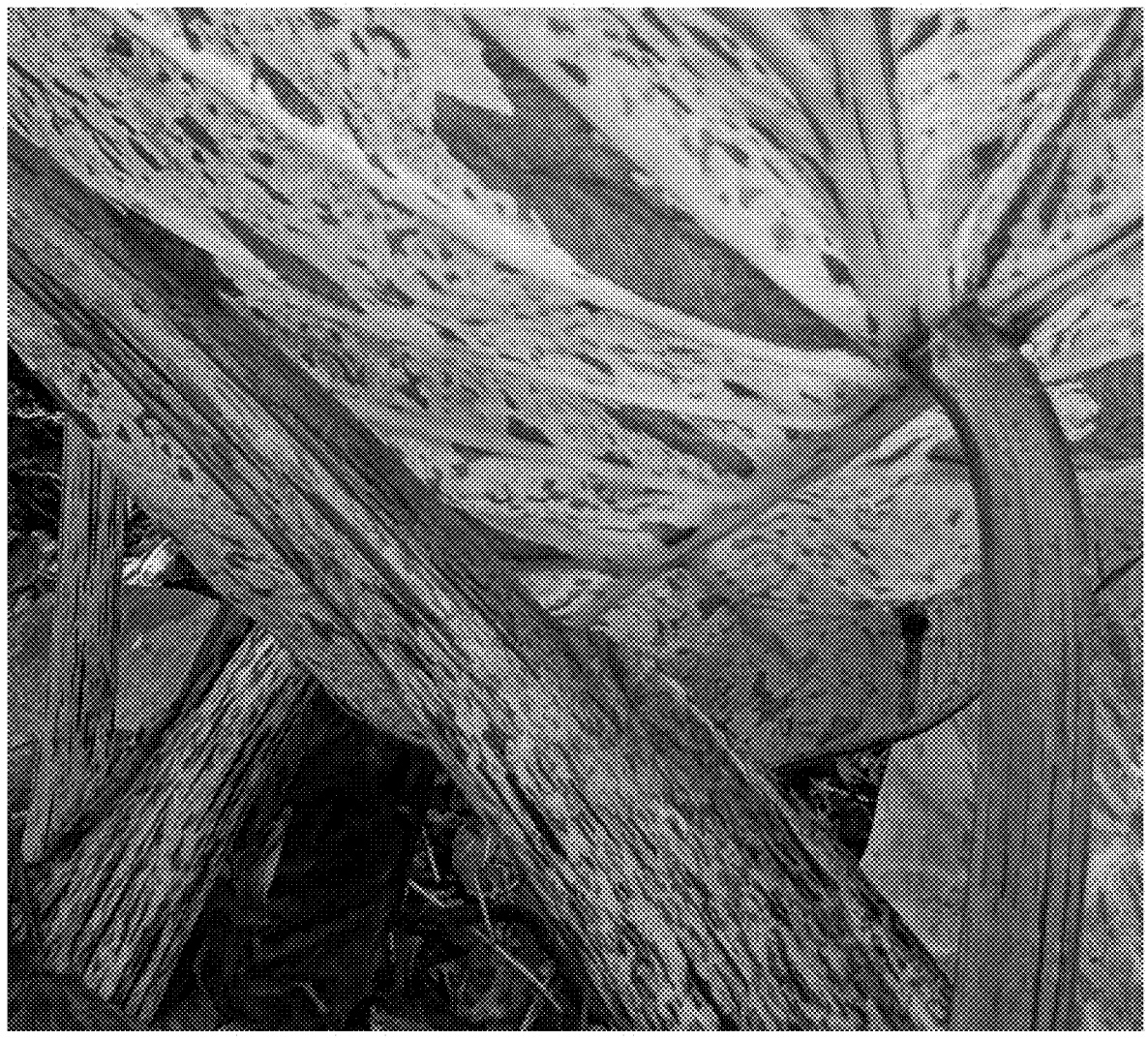
FIG. 3 shows the abaxial surface of a leaf of 'Tropical Paradise' with its younger burgundy-colored petiole. The figure also includes a depiction of an older petiole in which the purple-black striped variegation has become dominant.

The following is a detailed description of the new *Colocasia* plant named 'Tropical Paradise'. Data was collected from a plant which was 13 months old from planting a young liner plant directly in-ground with later mulching and drip irrigation as needed in order to maintain soil and root moisture and stimulate vigorous growth. The color determinations are in accordance with the 2001 edition of The Royal Horticultural Society Colour Chart, London, England, except where general color terms of ordinary dictionary significance are used.

Botanical classification:

*Family*.—Arecaceae (commonly Aroid).

*Genus*.—*Colocasia*.

*Species*.—*Esculenta*.

*Denomination*.—'Tropical Paradise'.

*Common name*.—Taro or elephant ears.

Plant:

*Plant use*.—Container or landscape plant.

*Cultural requirements*.—Consistently moist root zone, favored by mulching and drip irrigation. Position where plants will receive full sunshine except for shading from intense sun in dry conditions. Plants will thrive where night temperatures remain above 50° F. and day temperatures range between 70° F. and 80° F. or warmer.

*Roots* (*in-ground plant*).—System type: Tuberous. Tuber dimensions: 18 cm to 20 cm in length, 8 cm to 10 cm in diameter. Tuber color: 155B.

*Plant vigor* (*in-ground*).—Vigorous, prolific basal shoot production.

*Container production*.—A one-quart container plant may be produced and will exhibit its characteristic leaf colors and variegation patterns in approximately 8-10 weeks from planting a rooted plug or liner which has been grown in temperature range 18° C. to 20° C. for approximately 12 weeks from initial planting as a tissue cultured division or explant. A two-gallon container plant grown under similar conditions of temperature and moisture may be produced in approximately 12-16 weeks.

*Plant dimensions* (*mature plants in ground*.—1 m in height, 1 m in maximum width (leaf canopy).

*Plant hardiness*.—USDA Zone 7b.

*Propagation*.—Propagation is accomplished by huli propagation and by tissue culture.

*Pest or disease susceptibility and resistance*.—'Tropical Paradise' has not been found to be more or less susceptible to disease or pests than other cultivars of the genus.

Parentage:

*Male parent*.—*Colocasia* seedling 'FO7' (unpatented).

*Female parent*.—*Colocasia* seedling 'MG-Mojito' (unpatented).

Foliage:

*Leaf number*.—A mature plant of 'Tropical Paradise' bears 12 to 15 opening and open leaves at one time. New shoots (petioles) bearing new leaves appear rapidly, around every 2 to 3 days, when plants are grown with consistent moisture and in sunny conditions and in warm nights.

*Leaf*.—

*Dimensions at maturity* (*largest observed on container plant*).—Leaf length from line of apex of leaf lobe base to leaf apex: 32 cm. Leaf width (maximum): 22 cm. Depth of leaf sinus: Ranges between 8.5 cm and 9.5 cm.

*Aspect*.—Arching downwards at 45° below horizontal.

*Shape*.—Rounded, sagittate.

*Margins*.—Smooth, entire, undulating between adjacent lateral veins.

*Marginal band.*—Narrow (1 mm) margin band, color grey-green N189A, extending 1 mm occupying the entire margin including leaf sinus.

*Apex.*—Sub-acute.

*Base.*—Auriculate, bilobed.

*Leaf attachment.*—Petiolate with characteristic tissue formed on the adaxial surface opposite the junction of abaxial leaf surface with the upper termination of the petiole. This area of the leaf tissue is known as the "piko". The principal veins of both leaf surfaces radiate from the piko.

Leaf texture, color, variegation (adaxial surface):

*Leaf ground texture, color (adaxial surface).*—Texture glossy, background color bright yellow-green N144B overlaid with discrete dark green 136A or dark grey-green N189A flecks or patches.

*Variegation (adaxial surfaces).*—Flecks or patches.

*Variegation dimensions (smaller flecks).*—Predominantly approximately 2 cm in length and 5 mm in width.

*Variegation dimensions (larger patches).*—Irregularly shaped, often adjacent to sections of leaf margin, extending inwards up to 6 cm from margin.

Leaf texture, color, variegation (abaxial surface): Texture dull, matte, background color light grey-green 191B, variegations (flecks or patches) as adaxial surface, color grey-purple N187C.

Veins, adaxial surface:

*Number.*—3 principal veins radiate from the piko, of which one central vein is longer and wider and descends from piko to leaf apex.

*Central principal vein dimensions.*—30 cm-32 cm in length, 4 mm-5 mm in width towards piko, 2 mm-3 mm in width towards margin.

*Upper principal veins (pair) dimensions.*—18 cm-20 cm in length, 5 mm-6 mm in width at piko reducing to 2 mm-3 mm in width at leaf margin.

*Principal veins color.*—Predominantly pale green-white 157D except for infused red-purple longitudinal stripes, color 60D, as Piko color.

*Vein profile.*—Shallowly depressed at surface.

Veins, abaxial surface:

*Number.*—3 principal veins radiate from the piko, of which one central vein is longer and wider and descends from piko to leaf apex. Lateral veins narrow.

*Central vein dimensions.*—30 cm-32 cm in length, 4 mm-5 mm in width towards piko, 2 mm-3 mm in width towards margin.

*Lateral vein dimensions.*—11 cm in length, 3 mm-4 mm in width.

*Abaxial principal vein color.*—Uniformly yellow-green 152A.

*Abaxial principal vein profile.*—Raised and rounded. Midvein height 4 mm towards piko, and lower, 1 mm-2 mm towards margin.

Abaxial petioles:

*Shape.*—Terete.

*Dimensions.*—Length 45 cm, diameter 1 cm-1.5 cm at base, reducing to 8 mm-9 mm at abaxial surface leaf attachment.

*Surface.*—Semi-glossy.

*Color (on recently formed leaves).*—Grey-purple to burgundy, ranging between 184A and 187A.

*Color (on mature and older leaves).*—Massed purple-black (between N186A and 202A) stripes almost obscuring light cream-green 157B background petiole color.

Piko (adaxial surface only):

*Piko shape and dimensions (adaxial leaf surface only).*—Irregular at junction of midvein and upper veins.

*Piko coloration.*—Red purple coloration 60D extends as longitudinal stripes from center of piko and into and along each of the principal veins.

Inflorescence: None observed.

Flowers and reproductive organs: None observed.

Seed: Seed is not produced naturally since male and female flowers within each inflorescence do not mature at the same time. Pollination can be achieved manually or in nature, only with the presence of small insect pollinators which are found in regions of genetic origin of the species, and not Hawaii.

COMPARISON TO PARENTAL LINES

Whereas the leaves of 'Tropical Paradise' and the male parent 'FO7' are similarly glossy in texture, the leaves of 'Tropical Paradise' are variegated light yellow-green whilst the leaves of 'FO7' are uniformly light green in color, without any variegation.

Whereas the leaves of the female parent 'MG-Mojito' are matte in texture, the leaves of 'Tropical Paradise' are glossy.

'Tropical Paradise' is further distinguished from its parents by the colors of their respective petioles. The petioles of 'Tropical Paradise' are burgundy-colored while young and markedly variegated with purple-black stripes as the leaves and petioles age. The petioles of the male parent 'FO7' are light green in color with occasional darker green longitudinal stripes. The petioles of the female parent 'MG-Mojito' are light green in color with purple longitudinal stripes'.

COMPARISON TO PARENTAL LINES AND COMMERCIAL VARIETY

The closest comparison variety in commerce known to the inventor is the male parent *Colocasia* 'Mojito' (U.S. Plant Pat. No. 21,995). Whereas the leaves of 'Tropical Paradise' are glossy and light yellow-green in color overlaid with flecks and patches of darker green variegation, the leaves of 'Mojito' are matte, and green, dark green to black in color. In addition, the petioles of 'Tropical Paradise' are burgundy-colored while young and markedly variegated with purple-black stripes as the leaves and petioles age. The petioles of 'Mojito' are red-purple in color and bear very dark purple-black longitudinal streaked and striped variegation.

I claim:

1. A new and distinct variety of *Colocasia* plant named 'Tropical Paradise' as illustrated and described herein.

* * * * *